US010940140B2

(12) United States Patent
Durham

(10) Patent No.: US 10,940,140 B2
(45) Date of Patent: Mar. 9, 2021

(54) PHARMACEUTICAL COMPOSITION FOR THE TREATMENT OF AUTISM

(71) Applicant: Stalicla S.A., Geneva (CH)

(72) Inventor: Lynn Durham, Geneva (CH)

(73) Assignee: Stalicla S.A., Geneva (CH)

( * ) Notice: Subject to any disclaimer, the term of this patent is extended or adjusted under 35 U.S.C. 154(b) by 0 days.

(21) Appl. No.: 16/182,553

(22) Filed: Nov. 6, 2018

(65) Prior Publication Data

US 2019/0134011 A1 May 9, 2019

Related U.S. Application Data

(60) Provisional application No. 62/582,141, filed on Nov. 6, 2017, provisional application No. 62/663,647, filed on Apr. 27, 2018.

(30) Foreign Application Priority Data

Nov. 6, 2017 (EP) .................................. 17200219
Apr. 27, 2018 (EP) .................................. 18169952

(51) Int. Cl.
*A61K 31/437* (2006.01)
*A61P 25/00* (2006.01)
*A61K 31/015* (2006.01)
*A61K 45/00* (2006.01)

(52) U.S. Cl.
CPC .......... *A61K 31/437* (2013.01); *A61K 31/015* (2013.01); *A61K 45/00* (2013.01); *A61P 25/00* (2018.01)

(58) Field of Classification Search
CPC .............................. A61K 31/015; A61K 31/437
See application file for complete search history.

(56) References Cited

U.S. PATENT DOCUMENTS

| 2005/0282896 A1* | 12/2005 | Lopaschuk | A61K 31/19 |
| | | | 514/557 |
| 2014/0011745 A1* | 1/2014 | Dobson | A01N 1/0226 |
| | | | 514/18.5 |
| 2015/0093458 A1* | 4/2015 | Sher | A23L 33/10 |
| | | | 424/764 |
| 2016/0193161 A1* | 7/2016 | Hill | A61K 31/325 |
| | | | 424/133.1 |

FOREIGN PATENT DOCUMENTS

EP 17200185 5/2013
WO WO-0020592 A1 * 4/2000 ......... A01K 67/0275

OTHER PUBLICATIONS

Yoon et al (FEBS Open Bio, online Nov. 2014, vol. 5, pp. 20-25) (Year: 2014).*
Beraldo et al (Journal of Cell Biology, 2005, vol. 170, pp. 551-557) (Year: 2005).*
Zhao et al (Journal of Pineal Research, Feb. 2017, vol. 62) (Year: 2017).*
Wong et al (Gynecologic Oncology, 2008, vol. 109, pp. 394-402; abstract) (Year: 2008).*
U.S. Pharmacopeia National Formulary, pp. 1857-1859 (1990).

* cited by examiner

*Primary Examiner* — Mark V Stevens
(74) *Attorney, Agent, or Firm* — Millen White Zelano and Branigan, PC; Csaba Henter

(57) ABSTRACT

The present invention relates to a pharmaceutical composition or a kit comprising, a first substance capable of raising intracellular cAMP levels, and a second substance capable of modulating intracellular calcium concentration.

Likewise, the present invention relates to methods of treating patients suffering from autism spectrum disorder (ASD) phenotype 1 by administering an effective amount of a substance capable of raising intracellular cAMP levels and, optionally, an effective amount of a substance capable of modulating intracellular calcium concentration.

2 Claims, No Drawings

PHARMACEUTICAL COMPOSITION FOR THE TREATMENT OF AUTISM

CROSS-REFERENCE TO RELATED PATENT APPLICATIONS

This application claims priority from EP 17200219.8, filed Nov. 6, 2017, EP 18169952.1, filed Apr. 27, 2018, Provisional Application 62/582,141, filed Nov. 6, 2017, and Provisional Application 62/663,647, filed Apr. 27, 2018, all of which are incorporated by reference in their entirety.

FIELD OF THE INVENTION

The invention relates to a pharmaceutical composition for treating the core symptoms of autism spectrum disorder (ASD) and/or associated symptoms including learning disabilities, language impairment and impairments in executive functioning that can be associated with the disease in patients with ASD—and preferably in phenotype 1 patients—a subcategory of patients presenting with specific differentiating clinical sets of signs and symptoms.

BACKGROUND OF THE INVENTION

Autism spectrum disorder (ASD) are a group of neurodevelopmental disorders frequently characterized by impairments in social interactions, difficulties with language and communication, and the presence of repetitive, perseverative behaviors. ASD typically appears during the first three years of life and manifests in characteristic symptoms or behavioral traits. A diagnosis of ASD currently includes several conditions that used to be diagnosed separately: autistic disorder, pervasive developmental disorder not otherwise specified (PDD-NOS), and Asperger syndrome. All of these conditions are now encompassed by the diagnostic criteria for autism spectrum disorder as set forth in the American Psychiatric Association's Diagnostic & Statistical Manual of Mental Disorders, Fifth Edition (DSM-5).

While ASD is currently defined by symptoms in core areas, there exists significant heterogeneity in genetics, phenotypes, clinical presentation, and associated comorbidities The genetic contribution to the causation/predisposition to autism is considered to be substantial on the basis of high concordance in monozygous twins s contribute 83% of the risk for ASD, and environmental factors thus seem to play a minor 17% though significant role in the developmental etiology of ASD. However, to further complicate matters, genetic and epigenetic factors intertwine with prenatal and lifelong dynamic environmental factors to influence individual patient pathogenesis. Nevertheless, causal genetic factors can only be identified in 15 to 20% of patients, and the vast majority ASD patients are still considered idiopathic.

A subgroup of ASD patients, the so called ASD phenotype 1 (see EP 17200185.1), shows an upregulation of pathways involved in adaptation to stress, apoptosis or cell differentiation, cell proliferation, cell cycle progression, cell division, and differentiation. In particular, but not limited to, the PI3K, AKT, mTOR, MAPK, ERK/JNK-P38 pathways have been implicated in autism. Patients diagnosed with ASD phenotype 1 also exhibit a significant increase in proinflammatory cytokines (TNF-α, IL-6, IL-1β, IL-17A, IL-22 and GM-CSF), Th1 cytokine (INF-γ) and chemokine (IL-8) expression in the brain compared to healthy control patients, whereas no significant differences between ASD phenotype 1 patients and normal controls were shown for the Th2 cytokines (IL-4, IL-5) and IL-10. Accordingly, the Th1/Th2 ratio may be significantly increased in the ASD Phenotype 1 patients.

Currently, there is no effective treatment for the ASD Phenotype 1 subgroup of patients. In fact, these patients react negatively to administration of antioxidant substances, despite the fact that these have been reported to improve some patients with autism.

Fragile X is the most common monogenetic cause of both intellectual disability and autism spectrum disorder. Patients with Fragile X syndrome (FXS), caused by loss of function of the fragile X mental retardation 1 (Fmr1) gene, often exhibit many of the symptoms commonly associated with ASD, such as developmental delays, communication impairments and anxiety.

Despite these studies of neurodevelopmental disorders such as ASD, ASD Phenotype 1, and Fragile X syndrome, there remains a need for novel treatments of neurodevelopmental disorders such as ASD, ASD phenotype 1, and Fragile X Syndrome.

SUMMARY OF THE INVENTION

The present invention meets this need by providing methods and pharmaceutical compositions or kits for treating patients diagnosed with an autism spectrum disorder (ASD), ASD phenotype 1, or fragile X syndrome.

In one aspect of the present disclosure, the pharmaceutical composition comprises
 a first substance capable of raising intracellular cAMP levels, and
 a second substance capable of modulating intracellular calcium concentration.

In some embodiments, the substance capable of raising intracellular cAMP levels is a PDE inhibitor. In some embodiments, the PDE inhibitor is a PDE4 inhibitor or a PDE4-3 dual inhibitor. In some embodiments, the PDE inhibitor is selected from the group consisting of theophylline, enprofylline, pentoxifylline, dyphylline, caffeine, dipyridamole, roflumilast, crisaborole, apremilast, cilomilast, tetomilast, rolipram, (S)-rolipram, (R)-rolipram, amrinone, milrinone, enoximone, daxalipram (R-mesopram), lirimilast, AWD-12-281, cipamfylline, oglemilast, tofimilast, CI-1044, HT-0712, MK-0873, arofylline, CI-1018, T-2585, YM-976, V-11294A, piclamilast, atizoram, filaminast, SCH 351591, IC-485, D-4418, CDP-840, and L-826,141. In some embodiments, the substance capable of raising intracellular cAMP levels comprises a substance capable of activating a G protein-coupled adenosine $A_{2A}$ receptor. In some embodiments, the substances capable of activating a G protein-coupled adenosine $A_{2A}$ receptor is selected from the group consisting of regadenoson, bidenoson, adenosine, 2-phenilaminoadenosine, 2-amino-4-(4-hydroxyphenyl)-6-[(1H-imidazol-2-ylmethyl)thio]-3,5-pyridinecarbonitrile, 4-[2-[(6-amino-9-b-D-ribofuranosyl-9H-purin-2-yl)thio]ethyl]benzenesulfonic acid ammonium salt, 2-hexynyl-5'-N-ethylcarboxamidoadenosine, CGS-21680, and UK-432,097.

In some embodiments, the substance capable of modulating intracellular calcium concentration comprises a retinoic acid-related orphan receptor-alpha (RORA) agonist. In some embodiments, the substance capable of modulating intracellular calcium concentration comprises a calcium channel inhibitor or an inhibitor of the solute carrier family 12 member 1, solute carrier family 12 member 1, 2, 4 or solute carrier family 12 member 1, 2, 4, 5. In some embodiments, the substance capable of modulating intracellular calcium concentration is selected from the group consisting of dihydropyridines, phenylakylamines, benzothiazepines, indolazines, aminoglycosides, and 4-substituted derivatives of sulfamoylbenzoic acid. In some embodiments, the 4-substituted derivative of sulfamoylbenzoic acid is a derivative of 4-substituted-3-amino-5-sulfamoylbenzoic acid.

In some embodiments, the derivative of 4-substituted-3-amino-5-sulfamoylbenzoic acid is selected from the group consisting of bumetanide, AqB007, AqB011, PF-2178, BUM13, BUM5, bumepamine, and mixtures thereof.

In some embodiments, the substance capable of modulating intracellular calcium concentration is selected from the group consisting of nifedipine, niludipine, nicardipine, nimodipine, NZ-105, amlodipine, felodipine, isradipine, diperdipine, emopamil, devapamil, verapamil, diltiazem, flunarizine, fluspirilene, pimozide, fantofarone, nicergoline, neomycin, gentamycin, kanamycin, cisapride, clopamide, cyproheptadine, loratadine, domperidone, fentanyl, alfentanil, sufentanil, flecainide, indoramin, isonepecotic acids, ketotifen, loperamide, mepivacaine, methylphenidate, minoxidil, nipecotic acid, paroxetine, pempidine, penfluridol, perhexiline, pipecolics acid, bupivacaine, cyclohexemide, thalidomide, terfenadine, trihexyphenidyl, clevidipine, lomerazine, fostedil, anipamil, torasemide, chlorthalidone, etacrynic acid, furosemide, trichlormethiazide, hydroflumethiazide, methylclothiazide, bumetanide, ibutilde, mibefradil, dronedarone, amiodarone, nisoldipine, nitrendipine, nilvadipine, gabapentine, and ambroxol hydrochloride.

In some embodiments, the substance capable of raising intracellular cAMP levels is ibudilast, and the substance capable of modulating intracellular calcium concentration is bumetanide. In some embodiments, A method of treating a patient diagnosed with Fragile X syndrome comprising administering to a patient in need thereof an effective amount of a pharmaceutical composition comprising a first substance capable of raising intracellular cAMP levels and an effective amount of a second substance capable of modulating intracellular calcium concentration.

In accordance with some embodiments, there are provided methods of treating a patient diagnosed with autism spectrum disorder (ASD) comprising administering to a patient in need thereof an effective amount of a pharmaceutical composition comprising a first substance capable of raising intracellular cAMP levels, and a second substance capable of modulating intracellular calcium concentration.

In another aspect, there are provided kits comprising
a first substance capable of raising intracellular cAMP levels, and
a second substance capable of modulating intracellular calcium concentration.

In some embodiments of the kit, the substance capable of raising intracellular cAMP levels is a PDE inhibitor. In some embodiments of the kit, the PDE inhibitor is a PDE4 inhibitor or a PDE4-3 dual inhibitor. In some embodiments of the kit, the PDE inhibitor is selected from the group consisting of caffeine, theophylline, enprofylline, pentoxifylline, dyphylline, theobromine, aminophylline, prepentofylline, L-reuteri, dipyridamole, cilostazol, etazolate, roflumilast, crisaborole resembrenone, drotaverin, ibudilast, apremilast, cilomilast, tetomilast, rolipram, (S)-rolipram, (R)-rolipram, amrinone, milrinone, enoximone, daxalipram (R-mesopram), lirimilast, AWD-12-281, cipamfylline, oglemilast, tofimilast, CI-1044, HT-0712, MK-0873, arofylline, CI-1018, T-2585, YM-976, V-11294A, piclamilast, atizoram, filaminast, SCH 351591, IC-485, D-4418, CDP-840, and L-826,14.

In some embodiments of the kit, the substance capable of raising intracellular cAMP levels is a substance capable of activating a G protein-coupled adenosine $A_{2A}$ receptor. In some embodiments of the kit, the substance capable of activating a G proteincoupled adenosine $A_{2A}$ receptor is selected from the group consisting of regadenoson, bidenoson, adenosine, 2-phenilaminoadenosine, 2-amino-4-(4-hydroxyphenyl)-6-[(1H)-imidazol-2-ylmethyl)thio]-3,5-pyridinecarbonitrile, 4-[2-[(6-amino-9-b-D-ribofuranosyl-9H-purin-2-yl)thio]ethyl]benzenesulfonic acid ammonium salt and 2-hexynyl-5'-N-ethylcarboxamidoadenosine, CGS-21680 and UK-432,097. In some embodiments of the kit, the substance capable of modulating intracellular calcium concentration is a retinoic acid-related orphan receptor-alpha (RORA) agonist In some embodiments of the kit, the substance capable of modulating intracellular calcium concentration is a calcium channel inhibitor or an inhibitor of the solute carrier family 12 member 1, an inhibitor of the solute carrier family 12 member 1, 2, 4 or an inhibitor of the solute carrier family 12 member 1, 2, 4, 5.

In some embodiments of the kit, the substance capable of modulating intracellular calcium concentration is selected from the group consisting of dihydropyridines, phenylakylamines, benzothiazepines, indolazines, aminoglycosides and a 4-substituted derivative of sulfamoylbenzoic acid. In some embodiments of the kit, the 4-substituted derivative of sulfamoylbenzoic acid is selected from the group consisting of bumetanide, AqB007, AqB11, PF-2178, BUM13, BUM5, bumepamine and mixtures thereof. In some embodiments of the kit, the 4-substituted derivative of sulfamoylbenzoic acid is a derivative of 4-substituted-3-amino-5-sulfamoylbenzoic acid.

In some embodiments of the kit, the substance that modulates intracellular calcium concentration is selected from the group consisting of nifedipine, niludipine, nicardipine, nimodipine, NZ-105, amlodipine, felodipine, isradipine, diperdipine, emopamil, devapamil, verapamil, diltiazem, flunarizine, fluspirilene, pimozide, fantofarone, nicergoline, neomycin, gentamycin, kanamycin, cisapride, clopamide, cyproheptadine, loratadine, domperidone, fentanyl, alfentanil, sufentanil, flecainide, indoramin, isonepecotic acids, ketotifen, lobeline, loperamide, mepivacaine, methylphenidate, minoxidil, nipecotic acid, paroxetine, pempidine, penfluridol, perhexiline, pipecolics acid, bupivacaine, cyclohexemide, thalidomide, terfenadine, trihexyphenidyl, clevidipine, lomerazine, fostedil, anipamil, torasemide, chlorthalidone, etacrynic acid, furosemide, trichlormethiazide, hydroflumethiazide, methylclothiazide, bumetanide, ibutilde, mibefradil, dronedarone, amiodarone, nisoldipine, nitrendipine, nilvadipine, gabapentine and ambroxol hydrochloride.

In some embodiments of the kit, the substance capable of raising intracellular cAMP levels comprises ibudilast and the substance capable of modulating intracellular calcium concentration comprises bumetamide.

In some embodiments, the kit disclosed herein is for use in the treatment of autism spectrum disorder (ASD). In some embodiments, the kit disclosed herein is for use in the treatment of Fragile X syndrome In another aspect, the methods disclosed herein is for treating patient exhibits characteristics consistent with being an ASD phenotype 1 patient. In some embodiments of the method for treating an ASD phenotype 1 patient, the substance capable of raising intracellular cAMP levels is a PDE inhibitor. In some embodiments of the method for treating an ASD phenotype 1 patient, the PDE inhibitor is a PDE4 inhibitor or a PDE4-3 dual inhibitor. In some embodiments of the method for treating an ASD phenotype 1 patient wherein the PDE inhibitor is ibudilast. In some embodiments of the method for treating an ASD phenotype 1 patient, the pharmaceutical composition is administered to the patient at a daily total dosage ranging from about 1-150 mg, preferably from about 10-80 mg, and more preferably from about 15-50 mg, divided among one, two, or three doses. In some embodiments of the method for treating an ASD phenotype 1 patient, the pharmaceutical composition is administered orally once, twice, or thrice daily to the patient using a dosage form that comprises 1, 5, 10, 15, 20, 25, 30, 35, 40, 45, or 50 mg ibudilast, or a pharmaceutically acceptable salt thereof.

In another aspect, there are provided methods of treating a patient diagnosed with autism spectrum disorder (ASD), wherein the treatment comprises
(i) determining whether the patient suffers from ASD phenotype 1, and
(ii) administering a therapeutically effective amount of a pharmaceutical composition comprising a first substance capable of raising intracellular cAMP levels, and a second substance capable of modulating intracellular calcium concentration to the patient if the patient suffers from ASD phenotype 1;
wherein determining whether the patient suffers from ASD phenotype 1 includes at least one step selected from
a) subjecting the patient to a challenge test with Nrf2-activator,
b) verifying for clinical signs of heightened expression of proliferation-associated pathways,
c) verifying for upregulation of Nrf2, or
d) verifying for low levels of protein kinase A; and
wherein it is determined that the patient suffers from ASD phenotype 1 if the patient exhibits at least one characteristic selected from negative behavioral response in the challenge test with a Nrf2 inducer, clinical signs of heightened expression of proliferation-associated pathways, upregulation of Nrf2, and low blood levels of protein kinase A.

DETAILED DESCRIPTION OF THE INVENTION

The present disclosure provides novel methods and compositions for treating patients diagnosed with autism spectrum disorder (ASD), in particular subtype ASD phenotype 1, and Fragile X syndrome. The herein disclosed methods, compositions and kits are based on the surprising discovery, illustrated in the Example herein, that the effect of substances capable of increasing intracellular cyclic adenosine monophosphate (cAMP) on treating cognitive dysfunctions associated with ASD can be synergistically and unexpectedly improved by co-treatment with substances capable of modulating intracellular calcium concentration. Accordingly, in one aspect, the present invention relates to a pharmaceutical composition or a kit comprising
a) a first substance capable of raising intracellular cAMP levels, and
b) a second substance capable of modulating intracellular calcium concentration.

The present disclosure is based on the surprising discovery, exemplified in the example herein, that ibudilast, a substance capable of raising intracellular cAMP levels, and bumetamide, a substance capable of modulating intracellular calcium concentration, in combination can treat patients diagnosed with ASD phenotype 1.

I. Definitions

Technical and scientific terms used herein have the meanings commonly understood by one of ordinary skill in the art to which the present invention pertains, unless otherwise defined. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

A "kit" is herein defined as combination product provided as a package and containing several individual parts that show a complementary effect when applied together. In this aspect, the effect achieved by a kit and a pharmaceutical composition are similar. A kit offers the advantage that dosage regimens of the individual parts may be adjusted to specific requirements and over time.

As used herein "subject," "patient," or "individual" refers to any subject, patient, or individual, and the terms are used interchangeably herein. When used in conjunction with "in need thereof," the term "subject," "patient," or "individual" intends any subject, patient, or individual having or at risk for a specified symptom or disorder.

As used herein, the term "administering" includes directly administering to another, self-administering, and prescribing or directing the administration of an agent as disclosed herein.

As used herein, the phrases "effective amount" and "therapeutically effective amount" mean that active agent dosage or plasma concentration in a subject, respectively, that provides the specific pharmacological effect for which the active agent is administered in a subject in need of such treatment. It is emphasized that an effective amount of an active agent will not always be effective in treating the conditions/diseases described herein, even though such dosage is deemed to be an effective amount by those of skill in the art.

As used herein, the term "pharmaceutical composition" refers to one or more active agents formulated with a pharmaceutically acceptable carrier, excipient or diluent.

The phrase "pharmaceutically acceptable" is employed herein to refer to those compounds, materials, compositions, and/or dosage forms which are, within the scope of sound medical judgment, suitable for use in vivo without excessive toxicity, irritation, allergic response, or other problem or complication, commensurate with a reasonable benefit/risk ratio.

II. Autism Spectrum Disorders

As used herein, the term "autism spectrum disorder (ASD)" is understood to cover a family of neurodevelopmental disorders characterized by deficits in social communication and interaction and restricted, repetitive patterns of behavior, interests or activities. In the following, the terms "autism spectrum disorder", "autism" and "ASD" are used interchangeably.

Herein, the terms "ASD phenotype 1" and "phenotype 1" are used interchangeably.

The term "ASD patient" is intended to cover not only humans diagnosed as having ASD, but also humans suspected of having ASD.

The person skilled in the art is well aware of how a patient may be diagnosed with ASD. For example, the skilled person may follow the criteria set up in "American Psychiatric Association; Diagnostic and Statistical Manual of Mental Disorders (DSM-5) Fifth edition" to give a subject a diagnosis of ASD. Likewise, ASD patients may have been diagnosed according to standardized assessments tools including but not limited to CIM-10, ICD-10, DISCO, ADI-R, ADOS or CHAT.

In other cases, patients may have a well-established DSM-IV diagnosis of autistic disorder, Asperger's disorder, or pervasive developmental disorder not otherwise specified (PDD-NOS).

Additionally, the present invention may be useful for subjects fulfilling one or more of the following criteria: persistent deficits in social communication and social interaction across multiple contexts as manifested by the following, currently or by history; restricted, repetitive patterns of behavior, interests, or activities, as manifested by at least two of the following, currently or by history; symptoms present in the early development period (but may not become fully manifest until social demands exceed limited capacities, or maybe masked by learned strategies in later life); symptoms cause clinically significant impairment in social, occupational, or other important areas of current functioning; these disturbances are not better explained by intellectual disability (intellectual development disorder) or global development delay.

ASD may occur with or without accompanying intellectual and/or language impairment. It may be associated with a known medical or genetic condition or an environmental factor or other neurodevelopmental, mental or behavioral disorders.

ASD may occur in different severity levels which may be classified according to impairment in social communication and in terms of restricted, repetitive behavior. Importantly, the term ASD phenotype 1 is not associated with a particular severity level of ASD. The present invention may be applied to patients suffering from any severity level of ASD.

Without being bound by a mechanism, it is believed that ASD patients can be characterized depending on whether or not they show an upregulation, a downregulation or normal levels of expression of biomolecular pathways involved in stress response.

Depending on whether and how the level of expression of these pathways in the respective individuals are modified, challenging ASD patients with Nrf2-activators which are known to upregulate the respective pathways will improve or worsen ASD symptoms.

In one aspect, the pharmaceutical composition or kit according to the present invention is for use in the treatment of an ASD or of a subgroup of ASD patients called ASD phenotype 1 patients.

ASD phenotype 1 patients may be identified with the help of a challenge test as described in non-published EP17200185.1, incorporated herein by reference in its entirety. Briefly, the concept of a challenge test is based on administration of an Nrf2-activator to an ASD patient. In ASD phenotype 1 patients, who already show an upregulation of the respective pathways, further activation of Nrf2 will lead to a worsening of core symptoms. Consequently, ASD phenotype 1 patients may be identified by a negative behavioral response to a challenge test.

Likewise, the skilled person can identify ASD phenotype 1 patient according to the clinical signs as defined in EP 17200185.1.

Another way of identifying ASD phenotype 1 patient is to check for upregulation of Nrf2. The person skilled in the art is well aware of how upregulation of the expression of a specific gene such as Nrf2 may be investigated. For example, it may be investigated at the mRNA level using quantitative PRC techniques such as qPCR or RT-qPCR. Likewise, upregulation of the expression of a gene may be determined on the protein level using protein quantification techniques such as Western Blot and quantitative dot blots. Upregulation is understood to mean an increase of mRNA levels or protein levels of at least 10% when compared to samples from healthy subjects.

Additionally, an ASD phenotype 1 patient may exhibit one or more of the following symptoms: increased levels of TH1 and pro-inflammatory sera cytokines (including but not limited to TNF-α, IL-1β, IL-6, Il-17A and IL-22) and/or of tissue expressions of mRNAs that encode inflammatory cytokines and/or excessive challenged T cell secretion of proinflammatory cytokines; upregulation of pathways involved in adaptation to stress, apoptosis, cell differentiation, cell proliferation, cell cycle progression, cell division and differentiation particular but not limited to PI3K, AKT, mTOR/MAPK, ERK/JNK-P38).

Currently, there remain a need for effective treatment available for patients diagnosed with autism spectrum disorders (ASDs), and in particular ASD phenotype 1. The present disclosure meets this need by providing a novel method of treating ASD and ASD phenotype 1 in particular by administering substances capable of raising intracellular cAMP levels and substances capable of modulating intracellular calcium concentration, which is unprecedented in the literature.

III. Pharmaceutical Compositions and Methods for Treatment of Autism.

The methods and compositions described herein are based on the surprising discovery that the effect of treating patients diagnosed with an autism spectrum disorder with substances capable of raising intracellular cyclic Adenosine Monophosphate (cAMP) levels can be synergistically and unexpectedly enhanced by co-treatment with substances capable of modulating intracellular calcium levels. This combined treatment with substances capable of raising intracellular cAMP and substances capable of modulating intracellular calcium levels is unprecedented in literature, and provides a novel method of treating autism spectrum disorders and fragile X syndrome.

a. Substances Capable of Raising Intracellular cAMP Levels

Cyclic Adenosine Monophosphate (cAMP) is synthetized from adenosine triphosphate (ATP) via the action of adenylyl cyclase (AC) and is converted to its inactive form 5'-adenosin monophosphate (5'-AMP) via hydrolysis by phosphodiesterase (PDE). Accordingly, one class of substances available for increasing cAMP levels is inhibitors of PDE.

In one aspect, the substance capable of increasing the intracellular levels of cAMP is a phosphodiesterase (PDE) inhibitor. Since phosphodiesterases convert cAMP to its inactive form, inhibiting phosphodiesterases will increase the levels of cAMP. One type of cAMP-PDEs is the PDE4 family which comprises four genes, PDE4A to D. PDE4s differ from other cAMP-PDEs by their kinetic properties and, particularly, their sensitivity to inhibition by the prototypical PDE4 inhibitor rolipram.

Accordingly, the present disclosure provides pharmaceutical compositions that comprises a substance that is capable of raising intracellular cAMP levels. The substance may be capable of raising intracellular cAMP levels directly or indirectly or both. A substance capable of directly raising intracellular cAMP levels may directly stabilize cAMP or inhibit degradation of cAMP. A substance capable of indirectly raising intracellular cAMP levels may activate molecules which lead to the generation of cAMP or may inhibit molecules degrading cAMP.

Inhibition is herein understood to mean blocking or reducing the activity of the respective molecule. In some embodiments, activity may be reduced by more than 20%, 30%, 40%, 50%, 60%, 70%, 80% or 90%. In a preferred embodiment, activity is reduced by at least 50%.

Activation is herein understood to mean upregulating or enhancing the activity of the respective molecule. In some embodiments, activity may be enhanced by more than 20%, 30%, 40%, 50%, 60%, 70%, 80% or 90%. In a preferred embodiment, activity may be enhanced by at least 50%.

Substances capable of inhibition of phosphodiesterase may be any molecule having a c-AMP-specific 3'-5'-cyclic phosphodiesterase 4A/B/C inhibitory effect, any molecule having a c-AMP 3'-5'-cyclic phosphodiesterase 4A/B inhibitory effect, any molecule having a cAMP 3'-5' phosphodiesterase 4A inhibitory effect, any molecule having a cAMP 3'-5'-cyclic phosphodiesterase 4A/B/C/D inhibitory effect, any molecule having a cAMP 3'-5'-cyclic phosphodiesterase 4A/B/D inhibitory effect, any molecule having a cAMP 3'-5' phosphodiesterase 4/B/D inhibitory effect, any molecule having a cAMP 3'-5'-cyclic phosphodiesterase 4D inhibitory effect, any molecule having a cAMP 3'-5'-cyclic phosphodiesterase 4B/D inhibitory effect, any molecule having a cAMP 3'-5'-cyclic phosphodiesterase 4B inhibitory effect.

Substances capable of inhibition of PDE include pyrazopyridines, preferably ibudilast, xanthines and derivatives, in particular enprofylline, pentoxifylline, dyphylline, aminophylline, propentofylline, preferably caffeine, theobromine, theophilline; flavonoids, in particular xanthohumol, leueocyanidol, delphinidin; flavones, in particular apigenin, luteolin; biflavones, in particular podocarpusflavone A; sequoiaflavones, in particular podocarpusflacvone B, 7,7''-dio-methylaminoflavone, bilobetin; flavanones, in particular dioclein, naringenin, hesperetin; stilbens, in particular E-(epsilon)-viniferin, curcumin; alkaloids, in particular chelerythrine, glaucine, apomorphine; aminopyrimidines and derivatives, in particular diakylarylamines, preferably dipyridamole; arenecarboxamides in particular benzamides, preferably roflumilast or piclamilast; benzoxaboroles, in particular crisaborole; isoindolones, in particular phthalimides, preferably apremilast; methoxybenzenes, in particular cilomilast; pyridinecarboxylic acids, in particular tetomilast; phenylpyrrolidines, in particular pyrrolidin-2-ones, preferably rolipram, (S)-rolipram, (R)-rolipram; bipyridines; oligopyridines, in particular amrinone, milrinone; arylphenylketones, in particular enoximone; oxazolidin-2-ones, in particular daxalipram (R-mesopram); probiotics, in particular L-reuteri.

In a preferred embodiment, the substance capable of inhibiting PDE is selected from the group consisting of ibudilast, caffeine, theobromine, theophylline, enprofylline, pentoxifylline, dyphylline, L-reuteri, dipyridamole, cilostazol, etazolate, roflumilast, crisaborole resembrenone, drotaverin, apremilast, cilomilast, tetomilast, rolipram, (S)-rolipram, (R)-rolipram, amrinone, milrinone, enoximone, daxalipram (R-mesopram), lirimilast, AWD-12-281, cipamfylline, oglemilast, tofimilast, CI-1044 ((R)—N-(9-amino-4-oxo-1-phenyl-3,4,6,7-tetrahydro-[1,4]diazepino[6,7,1-hi]indol-3-yl)nicotinamide), HT-0712 ((3S,5S)-2-Piperidinone, 5-(3-(cyclopentyloxy)-4-methoxyphenyl)-3-((3-methylphenyl)methyl), MK-0873 (3-(2-{3-[3-(cyclopropylcarbamoyl)-4-oxo-1,4-dihydro-1,8-naphthyridin-1-yl]phenyl}ethynyl)pyridin-1-ium-1-olate), arofylline, CI-1018 (N-(3,4,6,7-tetrahydro-9-methyl-4-oxo-1-phenylpyrrolo(3,2,1-jk)(1,4)benzodiazepin-3-yl)-4-Pyridinecarboxamide), T-2585 (2-{4-2,3-bis(hydroxymethyl)-6,7-diethoxy-1-naphthalenyl}-2-pyridinyl]-4-(3-pyridinyl)-1(2H)-phthalazinone), YM-976 (4-(3-chlorophenyl)-1,7-diethyl-1H,2H-pyrido[2,3-d]pyrimidin-2-one), V-11294A (3-(3-Cyclopentyloxy-4-methoxy-benzyl)-8-isopropyl-adenine), piclamilast, atizoram, filaminast, SCH 351591 (N-(3,5-Dichloro-1-oxido-4-pyridinyl)-8-methoxy-2-(trifluoromethyl)-5-quinolinecarboxamide), IC-485, D-4418 (N-(2,5-dichloro-3-pyridinyl)-8-methoxy-5-quinolinecarboxamide), CDP-840 (4-[(2R)-2-[3-(Cyclopentyloxy)-4-methoxyphenyl]-2-phenylethyl]-pyridine hydrochloride), L-826,141 (4-(2-(3,4-bis(difluoromethoxy)phenyl)-2-(4-(1,1,1,3,3,3-hexafluoro-2-hydroxypropan-2-yl)phenyl)ethyl)-3-methylpyridine 1-oxide), BPN14770 (2-(4-((2-(3-chlorophenyl)-6-(trifluoromethyl)pyrimidin-4-yl)amino)phenyl)acetamide), TDP101.

More preferred, the substance capable of inhibiting PDE is ibudilast.

Ibudilast is an anti-inflammatory and neuroprotective oral agent, metabolized mainly by the liver. Following administration of a single dose of 10 mg ibudilast to healthy adults, about 60% of the dose was excreted as metabolites in urine in 72 hours. The clinical efficacy of this product has been proven for bronchial asthma indication and cerebrovascular disorders. Ibudilast is currently under clinical trial in the U.S. for progressive multiple sclerosis and other conditions such as amyotrophic lateral sclerosis and substances dependence (codes: AV-411 or MN-166).

Substances that are capable of indirectly raising intracellular cAMP levels include substances capable of stimulating a G protein-coupled adenosine $A_{a2}$ receptor which activates adenylate cyclase, substances capable of activation of adenylate cyclase, substances that are capable of inhibiting glycogen synthetase kinase-3-beta (GSK-3-beta), as well as substances capable of inhibition of phosphodiesterase.

More specifically, a substance capable of activation of G protein-couple adenosine $A_{a2}$ receptor may be a purine nucleoside, in particular regadenoson, bidenoson, adenosine, 2-phenilaminoadenosine, 2-amino-4-(4-hydroxyphenyl)-6-[(1H-imidazol-2-ylmethyl)thio]-3,5-pyridinecarbonitrile, 4-[2-[(6-amino-9-b-D-ribofuranosyl-9H-purin-2-yl)thio]ethyl]benzenesulfonic acid ammonium salt, 2-hexynyl-5'-N-ethylcarboxamidoadenosine, CGS-21680 or UK-432,097.

Substances capable of inhibiting glycogen synthetase kinase-3-beta (GSK-3-beta) may be lithium salts.

b. Substances Capable of Modulating Intracellular Calcium Levels

The pharmaceutical composition according to the present invention may optionally comprise a substance capable of modulating intracellular calcium levels.

Herein, the term "modulating" may refer to a global decrease of cytosolic intracellular calcium, a localized increase of intracellular calcium in specific organelles, such as the mitochondria or endoplasmic reticulum, which in turns lead to a decrease of the cytosolic calcium concentration, or a modulation of the dynamics of intracellular calcium, such as a modulation of intracellular calcium vague, intracellular calcium oscillations, and/or intracellular calcium sparks.

The substance capable of modulating intracellular calcium levels may modulate intracellular calcium levels by mechanisms including either inhibition of intracellular calcium channels such as ryanodine receptor (RyR) or inositol-1,4,5-triphosphate-receptor (IP3R), or direct or indirect modulation of calcium-ATPase pumps, including Sarcoendoplasmic reticulum Ca2+ transport-ATPase (SERCA) and Plasma Membrane Ca2+ ATPase (PMCA), ionic exchangers, such as Na+/Ca2+ exchangers, Na+/H+ exchangers, Na+/K+ exchangers, NKKC or calcium channels.

The substance capable of modulating intracellular calcium levels may be any molecule having an inhibitory effect on solute carrier family 12 member 1, on solute carrier family 12 member 1,2,4 or on solute carrier family 12 member 1,2,4, 5.

Likewise, the substance capable of modulating intracellular calcium levels may be a molecule having an inhibitory effect on voltage-dependent calcium channels, preferably on voltage-dependent L-type, N-type or T-type calcium channels. In a preferred embodiment, the substance capable of modulating intracellular calcium levels may be a molecule having an inhibitory effect on voltage dependent L-type calcium channel subunits beta-1/-4, subunit beta-2 or subunits alpha-1/delta-2. The substance capable of modulating intracellular calcium levels may be a substance that inhibits the NKCC co-transporter.

In one embodiment, the substance capable of modulating intracellular calcium levels can be a diuretic. In another embodiment, the substance capable of modulating intracellular calcium levels can be an antiarrythmic agent. The skilled person is well aware of which drug or pharmaceuticals fall under the terms "diurectic" and "antiarrythmic agent".

In a preferred embodiment, the substance capable of modulating intracellular calcium levels may be selected from pyridinesulfonamides, in particular torasemide; isoindolines, in particular chlorthalidone; chlorophenoxyacetates, in particular etacrynic acid; aminobenzenesulfonamides, in particular furosemide and bumetanide; 4-substituted-3-amino-5-sulfamoylbenzoic acid derivatives, in particular but not limited to bumetanide, AqB007, AqB011, bumepamine; 1,2,4-benzothiadiazine-1,1-dioxides, in particular trichlormethiazide, hydroflumethiazide and methylclothiazide; dimethoxybenzenes, in particular ibutilde or verapamil; tetralins, in particular mibefradil; aryl-phenylketones, in particular dronedarone and amiodarone; 1,4-dihydropyridine and derivatives, in particular amlodipine, felodipine, diperdipine, nifedipine nimodipine, nisoldipine, nitrendipine, clevidipine, nicardipine and nilvadipine; benzoxadiazoles, preferably dihydropyridinecarboxylic acids and derivatives, in particular isradipine; diphenylmethylpiperazine and derivatives in particular flunarizine; heteroarylpiperidine in particular pimozide, domperidone; piperidines in particular cyproheptadine, fentanyl, alfentanil, sufentanil, flecainide, loperamide, methylphenidate, paroxetine, pempidine, perhexiline; henzocycloheptapyridine in particular loratadine; organic heterotetracyclic compound in particular nicergoline; aminoglycoside in particular, neomycin, gentamycin, kanamycin; piperidinecarboxamide in particular mepivacaine, bupivacaine; triptamines in particular indoramin; sulfonamides in particular clopamide; aminobenzamides in particular cisapride; aminopyrimidine in particular minoxidil; piperidine alkaloid in particular lobeline; piperidine antibiotic in particular cycloheximide non-proteinogenic amino acids such as gamma amino acids and derivatives, in particular gabapentin; piperidinemonocarboxylic acid in particular nipecotic acid, pipecolics acid; diarylmethane in particular penfluridol; benzothiazepine derivatives in particular diltiazem; phthalamides in particular thalidomide; diarylmethane in particular terfenadine, lomerazine, aromatic amine in particular ambroxol hydrochloride.

In another preferred embodiment, the substance capable of modulating intracellular calcium levels is selected from the group consisting of nifedipine, niludipine, nicardipine, nimodipine, NZ-105, amlodipine, felodipine, isradipine, diperdipine, emopamil, devapamil, verapamil, diltiazem, flunarizine, fluspirilene, pimozide, fantofarone, nicergoline, neomycin, gentamycin, kanamycin, cisapride, clopamide, cyproheptadine, loratadine, domperidone, fentanyl, alfentanil, sufentanil, flecainide, indoramin, isonepecotic acids, ketotifen, lobeline, loperamide, mepivacaine, methylphenidate, minoxidil, nipecotic acid, paroxetine, pempidine, penfluridol, perhexiline, pipecolics acid, bupivacaine, cyclohexemide, thalidomide, terfenadine, trihexyphenidyl, clevidipine, lomerazine, fostedil, anipamil, torasemide, chlorthalidone, etacrynic acid, furosemide, trichlormethiazide, hydroflumethiazide, methylclothiazide, bumetanide, ibutilde, mibefradil, dronedarone, amiodarone, nitrendipine, nilvadipine, gabapentine, ambroxol hydrochloride.

In yet another aspect, the pharmaceutical composition according to the present invention may optionally comprise a retinoic acid-related orphan receptor-alpha (RORA) agonist. RORA is a ligand dependent orphan nuclear hormone receptor that, in combination with co-regulator proteins, serves as a transcriptional regulator. RORA agonists may be phenylnaphthalenes, in particular adaptalene; sesquiterpenoids, in particular all-trans acitretin; diterpenoids, in particular alitretinoin or isotretinoin; thiochromanes, in particular tazarotene, retinoid esters, in particular etretinate; retinobenzoic acids, in particular tamibarotene, all-trans-retinoic acid or tretinoin. In a preferred embodiment, the RORA agonist may be selected from the group consisting of adapalene, all-trans retinoic acid, tretinoin, vitamin A, all-trans acitretin, alitretinoin, tazarotene, etretinate, isotretinoin, tamibarotene, LGD-1550, AM580 and Ch 55.

In sharp contrast, administering the pharmaceutical compositions according to the present invention, the effect of a substance capable of modulating intracellular calcium concentration such as bumetanide sets in within several days.

It is also envisaged by the present invention that the pharmaceutical composition according to the present invention additionally comprises pharmaceutically acceptable carriers or excipients such as lubricants, disintegrants, antiadherents, binders, preservatives, sorbents or vehicles.

In another aspect, the pharmaceutical composition according to the present invention may additionally comprise an agent that inhibits cell proliferation. In another aspect, the present invention relates to a pharmaceutical composition for use in the treatment of ASD phenotype 1, the pharmaceutical composition comprising a substance capable of raising intracellular cAMP levels.

In one embodiment, the substance capable of raising intracellular cAMP levels is preferably a PDE inhibitor. In a particularly preferred embodiment, the PDE inhibitor is ibudilast. Ibudilast may be administered to the patient at a daily total dosage ranging from about 1-150 mg, preferably from about 5-80 mg, and more preferably from about 15-50 mg, divided among one, two, or three doses. It may be administered orally once, twice, or thrice daily to the patient using a dosage form that comprises 1, 5, 10, 15, 20, 25, 30, 35, 40, 45, or 50 mg ibudilast or a pharmaceutically acceptable salt thereof.

In yet another aspect, the substance capable of modulating Ca2+ is a NKKC1 inhibitor. The substance capable of modulating intracellular calcium levels may be a substance that inhibits the NKCC co-transporter. NKCC co-transporters have been shown to promote rise in intracellular calcium either alone or in combination with other ions exchangers, such as Na/Ca exchanger, Na+/H+ exchanger, and/or Na+/K+ exchanger.

In a particularly preferred embodiment, the NKKC1 inhibitor is bumetanide. Bumetanide may be administered to the patient at a daily total dosage ranging from about 0.5 to 10 mg, preferably from 1 to 6 mg, and more preferably from 2 mg to 4 mg, divided into one, two, or three doses. It may be administered orally once, twice, or thrice daily to the patient using a dosage form that comprises 0.5, 1, 2 mg bumetanide, or a pharmaceutically acceptable salt thereof. Administration of a single dose may enhance patient compliance, while administration of several smaller doses ensures constant serum levels.

In yet another aspect, the pharmaceutical composition or kit according to the present invention may additionally comprise an agent that inhibits cell proliferation, such as compounds targeting PI3K, AKT, mTOR, MAPK, ERK/JNK-P38 known to modulate cellular proliferation.

In yet another aspect, the present invention relates to a pharmaceutical composition for use in the treatment of ASD in a patient, comprising a substance capable of raising intracellular cAMP levels, and a substance capable of modulating intracellular calcium levels, wherein the treatment comprises:
  (i) determining whether the patient suffers from ASD phenotype 1, and
  (ii) administering a therapeutically effective amount of the pharmaceutical composition to the patient if the patient suffers from ASD phenotype 1;
  wherein determining whether the patient suffers from ASD phenotype 1 includes at least one selected from:
  a) subjecting the patient to a challenge test with Nrf2-activator,
  b) verifying for clinical signs of heightened expression of proliferation associated pathways,
  verifying for upregulation of Nrf2, or
  verifying for low blood levels of protein kinase A; and
  wherein it is determined that the patient suffers from ASD phenotype 1 if he shows at least one of the following: negative behavioral response in a challenge test with a Nrf2 activator such as sulforaphane; clinical signs of heightened expression of proliferation-associated pathways; upregulation of Nrf2 or low levels of protein kinase A.

In another aspect, the pharmaceutical composition according to the invention may be used for the treatment of Fragile X.

In another aspect, a method is disclosed for treating a patient diagnosed with Fragile X Syndrome comprising administering to a patient in need thereof an effective amount of ibudilast or a pharmaceutically acceptable salt thereof.

In another aspect, a method is disclosed for treating a patient diagnosed with autism spectrum disorder (ASD) comprising administering to a patient in need thereof an effective amount of ibudilast or a pharmaceutically acceptable salt thereof.

In another aspect, a method is disclosed in which the patient exhibits characteristics consistent with being an ASD subtype 1 patient.

In another aspect, a method is disclosed in which ibudilast or a pharmaceutically acceptable salt is administered to the patient at a daily total dosage ranging from about 1-150 mg, preferably from about 10-80 mg, and more preferably from about 15-50 mg, divided among one, two, or three doses.

In another aspect, a method is disclosed in which ibudilast or a pharmaceutically acceptable salt thereof is administered orally once, twice, or thrice daily to the patient using a dosage form that comprises 1, 5, 10, 15, 20, 25, 30, 35, 40, 45, or 50 mg ibudilast or a pharmaceutically acceptable salt thereof.

IV. Pharmaceutical Composition Carriers and Dosage Forms

In some embodiments, a pharmaceutical composition disclosed herein comprises one or more pharmaceutically acceptable carriers, such as an aqueous carrier, buffer, and/or diluent.

In some embodiments, a pharmaceutical composition disclosed herein further comprises a simple polyol compound, such as glycerin. Other examples of polyol compounds include sugar alcohols. In some embodiments, a pharmaceutical composition disclosed herein comprises an aqueous carrier and glycerin at about a 2:1 ratio.

The pharmaceutical composition may conveniently be presented in unit dosage form and may be prepared by any of the methods well known in the art of pharmacy. An exemplary oral dosage form is a tablet or capsule. An exemplary intranasal dosage form is a liquid or powder nasal spray. A nasal spray is designed to deliver drug to the upper nasal cavity, and can be a liquid or powder formulation, and in a dosage form such as an aerosol, liquid spray, or powder.

The pharmaceutical composition herein may be combined or coordinately administered with a suitable carrier or vehicle depending on the route of administration. As used herein, the term "carrier" means a pharmaceutically acceptable solid or liquid filler, diluent or encapsulating material. A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations.

Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfanic. Examples of flavoring agents are Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutical used for therapeutic administration can be sterile. Sterility is readily accomplished by for example filtration through sterile filtration membranes (e.g., 0.2 micron membranes). Any pharmaceutically acceptable sterility method can be used in the compositions of the invention.

The pharmaceutical composition comprising a first substance capable of increasing cAMP levels, and optionally, a second substance capable of increasing intracellular calcium levels, or derivatives or salts thereof, will be formulated and dosed in a fashion consistent with good medical practice, taking into account the clinical condition of the individual patient, the method of administration, the scheduling of administration, and other factors known to practitioners.

EXAMPLE

A pharmaceutical composition comprising ibudilast and bumetanide was administered to patients with a diagnosis of autism spectrum disorder as defined in the DSM-5, or PDD-NOS or Asperger syndrome as defined in the DSM-IV.

Eligibility criteria: male sex, age 5-50, no current chronic illness, no history of active seizures within 1 year, normal liver, renal and thyroid function. Concomitant medications were permitted if doses were stable for at least 60 days prior to the initiation of the challenge test. Patients with no syndromic or identified genetic etiology.

Individuals with idiopathic ASD were classified as Phenotype 1 if they showed:
at least 1 mandatory characteristic:
  enlarged head size versus control population characterized by at least one standard deviations above the mean head circumference at 24 months and/or formal macrocephaly (HC>97% of the general population)
  and/or
  cyclical aggravation of core or ancillary autism symptoms potentiated by periods of infectious events, deciduous tooth loss, post-traumatic injury, endogenous and exogenous temperature variation
  and
at least 2, and most preferably at least 3 of the following 20 characteristics:
  accelerated hair and nail growth versus control population,
  increased tendency to present with lighter colors of skin and eyes as compared to individuals of the same ethnicity,
  substantially longer eyelashes than control subjects of the same ethnicity,
  at least 5 non-contiguous areas of hypopigmented skin, particularly presenting on the back of the patient,
  signs of edema during periods of infectious events, deciduous tooth loss, post-traumatic injury, or endogenous and exogenous factors modifying body temperature; more specifically, facial edema located in the periorbital and forehead areas,
  increased blood levels of gamma-glutamyl transpeptidase (GGT) as compared to typically developing individuals of the same age and ethnicity,
  congenital genitourinary malformations and/or functional impairment to initiate urinating,
  hypoplasia of the patella,
  frequent episodes of diarrhea specifically before the age of 5 years,
  frequent episodes of tinnitus,
  thinning of the corpus callosum,
  positive family history for hematological malignancies in particular but not limited to myeloma and acute promyelocytic leukemia,
  positive family history for rheumatoid arthritis, that is at least two affected first-degree relatives in two consecutive generations,
  adverse events in response to acetyl-salicylic acid or its derivatives,
  iris coloboma, either monolateral or bilateral,
  sleep hyperhidrosis particularly in newborns, toddlers and young children (notably increased night sweating during infancy and childhood—often reported by relatives to requires bed linen changes),
  increased Th1/Th2 ratio (i.e. elevated levels of Interleukin 1 beta, Interleukin 6, TNF-alpha, Interferon gamma),
  congenital accessory or duplicated spleen,
  congenital absence of the cisterna chili,
  reported history of mother suffering from viral or bacterial infection during pregnancy and/or biologically confirmed Maternal immune activation during pregnancy.

First Intervention

Description: Four of the patients characterized as above were administered ibudilast. The four subjects had varying levels of functioning ranging from mild to severe, and varying different levels of verbal and intellectual abilities. IQ values ranged from 61 to 86. All were males.

TABLE 1

Patient status prior to intervention

| ADI baseline score | Patient 1 | Patient 2 | Patient 3 | Patient 4 |
|---|---|---|---|---|
| ADI-r SI | 28 | 20 | 14 | 27 |
| ADI-r C | 24 | 19 | 18 | 17 |
| ADI-r RI | 7 | 5 | 7 | 7 |

Four patients were treated with ibudilast at a daily total dosage of 0.6 mg/kg, TID.

TABLE 2

Patient status after treatment for four weeks of treatment with ibudilast.

| ADI baseline score | Patient 1 | Patient 2 | Patient 3 | Patient 4 |
|---|---|---|---|---|
| ADI-r SI | 21 | 16 | 12 | 22 |
| ADI-r C | 20 | 15 | 14 | 14 |
| ADI-r RI | 6 | 5 | 5 | 7 |

After between two and four months of mono-treatment with ibudilast, loss of treatment efficacy was reported in all four patients with gradual return to pre-treatment baseline scores.

A new treatment regimen was introduced, this time ibudilast at a daily total dosage of 0.6 mg/kg, TID, was administered in conjunction with bumetanide at a daily total dosage of 0.08 mg/kg, BID (with a maximum upper daily dose of 2 mg/kg/day).

Following a mean length of administration of 8 days of bi-therapy treatment effect on reduction of ADI-r scores reflected restoration of initial monotherapy efficacy.

TABLE 3

Patient status after treatment for 8 days with ibudilast + bumetanide

| ADI baseline score | Patient 1 | Patient 2 | Patient 3 | Patient 4 |
|---|---|---|---|---|
| ADI-r SI | 20 | 15 | 11 | 22 |
| ADI-r C | 20 | 13 | 14 | 14 |
| ADI-r RI | 7 | 5 | 6 | 5 |

What is claimed is:

1. A pharmaceutical composition comprising
   (i) a first substance capable of raising intracellular cAMP levels in human neuronal cells, which is ibudilast, and
   (ii) a second substance capable of modulating intracellular calcium concentration in human neuronal cells, which is bumetanide,
   wherein the composition does not comprise any additional active ingredients other than ibudilast and bumetanide.
2. The pharmaceutical composition according to claim 1, which is in the form of a tablet or capsule suitable for oral administration to a human, which consists of said first substance and said second substance as active ingredients and one or more pharmaceutically acceptable carriers, excipients and/or diluents.

* * * * *